United States Patent [19]

Grollier et al.

[11] Patent Number: 4,638,822

[45] Date of Patent: Jan. 27, 1987

[54] HAIR-SETTING PROCESS

[75] Inventors: Jean-Francois Grollier; Claire Fiquet; Chantal Fourcadier, all of Paris; Claude Dubief, Le Chesnay; Daniele Cauwet, Paris, all of France

[73] Assignee: L'Oreal, Paris, France

[21] Appl. No.: 516,052

[22] Filed: Jul. 21, 1983

[30] Foreign Application Priority Data

Jul. 21, 1982 [LU] Luxembourg .............................. 84286

[51] Int. Cl.$^4$ .......................... A45D 7/04; A61K 7/09; A61K 7/11
[52] U.S. Cl. ............................................ 132/7; 424/47; 424/70; 424/71; 424/DIG. 1; 424/DIG. 2
[58] Field of Search ................... 132/7; 424/70, 71, 47, 424/DIG. 1, DIG. 2, 78, 81

[56] References Cited

U.S. PATENT DOCUMENTS

| 4,240,450 | 12/1981 | Grollier et al. | 424/DIG. 2 |
| 4,273,760 | 6/1981 | Koehler et al. | 424/70 |
| 4,445,521 | 5/1984 | Grollier et al. | 424/DIG. 1 |

FOREIGN PATENT DOCUMENTS 2383660 10/1978 France .
2436213 4/1980 France .

Primary Examiner—W. J. Shine
Attorney, Agent, or Firm—Fleit, Jacobson, Cohn & Price

[57] ABSTRACT

The invention relates to a hair-setting process which consists of applying to the hair, in a first stage, at least one cationic polymer and at least one anionic polymer in a solvent medium, then drying the hair thus treated, and wetting or rinsing the dried hair immediately after drying with an aqueous composition and setting and drying the hair.

35 Claims, No Drawings

HAIR-SETTING PROCESS

The present invention relates to a hair-setting process which employs a composition containing at least one cationic polymer and at least one anionic polymer.

We have already described in French Pat. No. 2,383,660 the use of compositions based on a cationic polymer and an anionic polymer for treating keratin materials.

These compositions make it possible to obtain easy disentangling and a pleasant touch in wet hair, and sheen, shape-retention and body in dried hair.

We have now discovered that it is possible to improve hair firmness and to retain this effect with time, even after application of several shampoos, by drying hair which has been treated with the composition containing a cationic polymer and an anionic polymer, before the hair is rinsed and set.

We have found in particular that by using this process it is possible to improve the shape-retention of the set with time and that this improvement in the shape-retention persists even after several shampoos.

This process also makes it possible to produce an appreciable increase in hair rigidity and to improve the disentanglement in an unexpected manner.

The present invention therefore provides a hair-setting process which consists in applying at least one cationic polymer and one anionic polymer to the hair, in drying the hair thus treated, in wetting or in rinsing the dried hair by means of an aqueous composition and in setting the hairstyle.

The hair-setting process according to the present invention is essentially characterised in that it consists in applying to the hair at least one cationic polymer and at least one anionic polymer in a solvent medium, in drying the hair thus treated, in wetting or in rinsing the dried hair, immediately after drying, with an aqueous composition and in setting and drying the hair.

The cationic and anionic polymers can be applied to the hair by means of a single composition containing them or by means of two compositions, one containing the cationic polymer and the other the anionic polymer, the compositions being applied consecutively without intervening rinsing.

In its preferred form the process according to the invention therefore comprises several stages which consist in:
- (a) applying a composition containing at least one anionic polymer and at least one cationic polymer,
- (b) drying the hair thus treated,
- (c) wetting or rinsing the hair with an aqueous composition immediately after drying,
- (d) setting and drying the hair.

Another variation of the process according to the invention consists in:
- (a) applying a composition containing a cationic polymer and then, without an intervening rinsing,
- (b) applying a composition containing an anionic polymer,
- (c) rinsing and then drying the hair,
- (d) rinsing or wetting the dried hair,
- (e) setting and drying the hair.

The invention can also be used in another embodiment:
- (a) by applying a composition containing an anionic polymer and then, without an intervening rinsing,
- (b) applying a composition containing a cationic polymer, the stages (c) to (e) being identical to those in the previous variation.

It is possible to carry out a rinsing before the drying in order to remove excess composition, but in all cases hair drying must be immediately followed by wetting or rinsing with a view to setting the hair.

The compositions employed in the first stage preferably contain, in addition to the cationic polymer and/or in addition to the anionic polymer, at least one electrolyte consisting of a salt of an alkali metal or an alkaline-earth metal.

These compositions do not, as a rule, contain any surface-active agent.

The cationic polymers used according to the invention are, in particular, polymers of the polyamine, polyaminopolyamide or poly-(quaternary ammonium) type, the amine or ammonium group forming part of a polymer chain or being joined thereto, and have molecular weights of 500 to 3,000,000.

Such polymers are described, in particular, in French Pat. Nos. and French patent application Nos. 2,077,143, 1,492,597, 2,162,025, 2,280,361, 2,252,840, 2,368,508, 1,583,363, 2,080,759, 2,190,406, 2,320,330, 2,270,846, 2,316,271, 2,336,434, 2,189,434 and 2,413,907, and U.S. Pat. Nos. 3,589,978, 4,031,307, 3,227,615, 2,961,347, 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

Polymers of this type which can be used according to the invention include:

(1) Vinylpyrrolidone/dialkylaminoalkyl acrylate or methacrylate copolymers (quaternised or unquaternised) such as those sold under the name Gafquat by Gaf Corp., for example "copolymer 845" and "Gafquat 734 or 755", described in greater detail in particular in French Pat. No. 2,077,143 and French patent application No. 2,393,573.

(2) Cellulose ether derivatives containing quaternary ammonium groups, such as those described in French Pat. No. 1,492,597 and in particular the polymers sold under the name JR, such as JR 125, JR 400 and JR 30 M, and under the name LR, such as LR 400 and LR 30 M, by the Union Carbide Corp., and cationic cellulose derivatives such as CELQUAT L 200 and CELQUAT H 100 sold by National Starch.

(3) Cationic polysaccharides such as those described in U.S. Pat. Nos. 3,589,978 and 4,031,307, and in particular Jaguar C. 13 s sold by Meyhall.

(4) Cationic polymers chosen from:
(a) polymers containing units of the formula:

$$-A-Z-Z- \qquad (I)$$

in which A denotes a radical containing two amino groups, preferably $$-N\overbrace{\phantom{XXX}}N-,$$

and Z denotes the symbol B or B'; B and B', which are identical or different, denote a divalent radical which is a straight-chain or branched-chain alkylene radical which contains up to 7 consecutive carbon atoms in the main chain, which is unsubstituted or substituted by one or more hydroxyl groups and which can also contain one or more oxygen, nitrogen and sulphur atoms and 1 to 3 aromatic and/or heterocyclic rings, the oxygen, nitrogen and sulphur atoms being present in the form of ether or thioether, sulphoxide, sulphone, sulphonium, amino, alkylamino, alkenylamino, benzylamino, amine oxide, quaternary ammonium, amido, imido, alcohol, ester and/or urethane groups; these polymers and the process for their preparation are described in French Pat. No. 2,162,025;

(b) polymers containing units of the formula:

in which A denotes a radical containing two amino groups, preferably

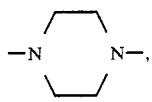

and $Z_1$ denotes the symbol $B_1$ or $B'_1$, at least one $Z_1$ denoting the symbol $B'_1$; $B_1$ denotes a divalent radical which is a straight-chain or branched-chain alkylene or hydroxyalkylene radical having up to 7 consecutive carbon atoms in the main chain, and $B'_1$ is a divalent radical which is a straight-chain or branched-chain alkylene radical which has up to 7 consecutive carbon atoms in the main chain, which is unsubstituted or substituted by one or more hydroxyl radicals and which is interrupted by one or more nitrogen atoms, the nitrogen atom being substituted by an alkyl chain which is optionally interrupted by an oxygen atom and which contains one or more hydroxyl groups; these polymers and the process for their preparation are described in French Pat. No. 2,280,361; and (c) the quaternary ammonium salts and the oxidation products of the polymers of the formulae indicated above under (a) and (b).

(5) Optionally alkylated, crosslinked polyaminopolyamides chosen from the group comprising at least one water-soluble crosslinked polymer obtained by crosslinking a polyaminopolyamide (A) prepared by the polycondensation of an acid compound with a polyamine. The acid compound is chosen from: (i) organic dicarboxylic acids, (ii) aliphatic monocarboxylic and dicarboxylic acids with a double bond, (iii) the esters of the abovementioned acids, preferably the esters with lower alkanols (having from 1 to 6 carbon atoms), and (iv) mixtures of these compounds. The polyamine is chosen from bis-primary, mono-secondary or bis-secondary polyalkylene-polyamines. Up to 40 mol% of this polyamine can be replaced by a bis-primary diamine, preferably ethylenediamine, or by a bis-secondary diamine, preferably piperazine, and up to 20 mol% can be replaced by hexamethylenediamine. The crosslinking is carried out by means of a crosslinking agent (B) chosen from epihalogenohydrins, diepoxides, dianhydrides, unsaturated anhydrides and bis-unsaturated derivatives. The crosslinking is characterised in that it is carried out by means of 0.025 to 0.35 mol of crosslinking agent per amine group of the polyaminopolyamide (A), generally by means of 0.025 to 0.2 and in particular by means of 0.025 to 0.1 mol of crosslinking agent per amine group of the polyaminopolyamide (A). These polymers and the process for their preparation are described in greater detail in French Pat. No. 2,252,840.

These crosslinked polymers are soluble in water to the extent of at least 10% without forming a gel, and the viscosity of a 10% strength solution in water at 25° C. is greater than 3 centipoises and usually from 3 to 200 centipoises.

The polyaminopolyamides (A) themselves can also be used according to the invention.

(6) Water-soluble crosslinked polyaminopolyamides obtained by crosslinking a polyaminopolyamide (A) (described above) by means of a crosslinking agent chosen from the group comprising:

(I) compounds of the group: (1) bis-halogenohydrins, (2) bis-azetidinium compounds, (3) bis-halogenoacyldiamines and (4) bis-(alkyl halides);

(II) oligomers obtained by reacting a compound (a) chosen from the group comprising (1) bis-halogenohydrins, (2) bis-azetidinium compounds, (3) bis-halogenoacyldiamines, (4) bis-(alkyl halides), (5) epihalogenohydrins, (6) diepoxides and (7) bis-unsaturated derivatives, with a compound (b) which is a difunctional compound reactive towards the compound (a); and (III) the quaternisation product of a compound (a) mentioned above or an oligomer (II) and containing one or more tertiary amino groups which can be totally or partially alkylated, with an alkylating agent (c) preferably chosen from methyl or ethyl chlorides, bromides, iodides, sulphates, mesylates or tosylates, benzyl chloride or bromide, ethylene oxide, propylene oxide or glycidol. The crosslinking is carried out by means of 0.025 to 0.35 mol, in particular by means of 0.025 to 0.2 mol and more particularly by means of 0.025 to 0.1 mol, of crosslinking agent per amine group of the polyaminopolyamide.

These crosslinking agents and these polymers, and also the process for their preparation, are described in French patent application No. 2,368,508.

(7) Polyaminopolyamide derivatives resulting from the condensation of polyalkylene-polyamines with polycarboxylic acids, followed by alkylation with one or more difunctional agents. Examples which may be mentioned are adipic acid/dialkylaminohydroxyalkyl-dialkylenetriamine polymers in which the alkyl radical contains from 1 to 4 carbon atoms and preferably denotes methyl, ethyl or propyl, which are described in French Pat. No. 1,583,363.

Amongst these derivatives, there may be mentioned the adipic acid/dimethylaminohydroxypropyl-diethylenetriamine polymers sold under the name Cartaétine F, F$_4$ or F$_8$ by SANDOZ.

(8) Polymers obtained by reacting a polyalkylene-polyamine containing two primary amine groups and at least one secondary amine group with a dicarboxylic acid which is diglycolic acid or a saturated aliphatic dicarboxylic acid having from 3 to 8 carbon atoms, the molar ratio of the polyalkylene-polyamine to the dicarboxylic acid being from 0.8:1 to 1.4:1, and the resulting polyaminopolyamide being reacted with epichlorohydrin in a molar ratio of epichlorohydrin to the secondary amine groups of the polyaminopolyamide of 0.5:1 to 1.8:1; these polymers are mentioned in U.S. Pat. Nos. 3,227,615 and 2,961,347.

The polymers of this type are, in particular, that sold under the name HERCOSETT 57 by Hercules Incorporated, which has a viscosity at 25° C. of 30 cps in 10% strength aqueous solution, and that sold under the name PD 170 or DELSETTE 101 by Hercules in the case of the adipic acid/epoxypropyl-diethylenetriamine copolymer.

(9) Cyclic polymers having a molecular weight of 20,000 to 3,000,000, such as homopolymers containing, as the main constituent of the chain, units corresponding to the formula (III) or (III'):

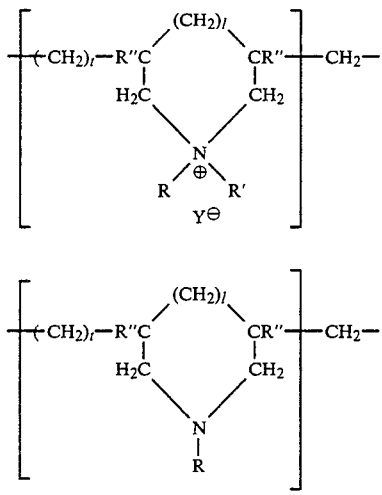

(III)

(III')

in which l and t are equal to 0 or 1 with the sum l+t=1, R'' denotes hydrogen or methyl, R and R' independently of one another denote an alkyl group having from 1 to 22 carbon atoms, a hydroxyalkyl group in which the alkyl group preferably has 1 to 5 carbon atoms, or a lower amidoalkyl group, or R and R' denote, together with the nitrogen atom to which they are attached, a heterocyclic group such as piperidinyl or morpholinyl, and also the copolymers containing units of the formula III or III' and units derived from acrylamide or from diacetone-acrylamide, and $Y^{\ominus}$ is an anion such as bromide, chloride, acetate, borate, citrate, tartrate, bisulphate, bisulphite, sulphate or phosphate.

Amongst the quaternary ammonium polymers of the type defined above, there may be mentioned the dimethyldiallylammonium chloride homopolymer sold under the name MERQUAT 100, which has a molecular weight of less than 100,000, and the dimethyldiallylammonium chloride/acrylamide copolymer having a molecular weight of more than 500,000, which is sold under the name MERQUAT 550 by MERCK.

These polymers are described in French Pat. No. 2,080,759 and its certificate of addition No. 2,190,406.

(10) Poly-(quaternary ammonium) compounds containing repeat units of the formula:

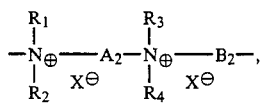

(IV)

in which $R_1$ and $R_2$, and $R_3$ and $R_4$, which are identical or different, represent an aliphatic, alicyclic or arylaliphatic radical containing at most 20 carbon atoms, or a lower hydroxyaliphatic radical or alternatively $R_1$ and $R_2$, and/or $R_3$ and $R_4$, together form, with the nitrogen atom to which they are attached a heterocyclic ring optionally containing a second heteroatom other than nitrogen, or alternatively $R_1$, $R_2$, $R_3$ and $R_4$ each represents a group:

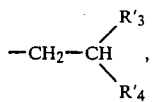

in which $R'_3$ denotes hydrogen or lower alkyl and $R'_4$ denotes one of the following groups:

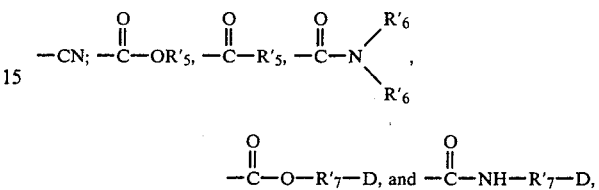

$R'_5$ denoting a lower alkyl group, $R'_6$ denoting hydrogen or a lower alkyl group, $R'_7$ denoting alkylene and D denoting a quaternary ammonium group, $A_2$ and $B_2$ independently represent an aliphatic group containing from 2 to 20 carbon atoms, which can be linear or branched and saturated or unsaturated and which can contain, inserted in the main chain, one or more aromatic rings, such as the group:

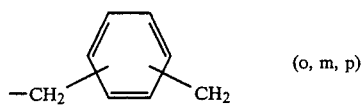

(o, m, p)

or one or more groups:

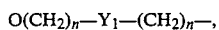

$Y_1$ denoting O, S, SO, $SO_2$,

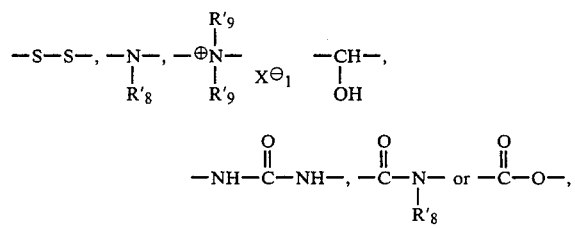

with $X_1^{\ominus}$ denoting an anion derived from a mineral or organic acid, n being 2 or 3, $R'_8$ denoting hydrogen or a lower alkyl group and $R'_9$ denoting lower alkyl, or alternatively $A_2$ and $R_1$ and $R_3$ together form a piperazine ring with the two nitrogen atoms to which they are attached; moreover, if $A_2$ denotes a linear or branched, saturated or unsaturated alkylene or hydroxyalkylene radical, $B_2$ can also denote a group:

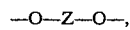

in which D denotes:
(a) a glycol radical of the formula

—O—Z—O—, in which Z denotes a linear or branched hydrocarbon radical or a group corresponding to the formula:

$$+CH_2-CH_2-O)_xCH_2-CH_2-$$

or $$+CH_2-CH-O)_yCH_2-CH- ,$$
$$\phantom{+CH_2-}CH_3 \phantom{-O)_yCH_2-}CH_3$$

in which x and y independently denote an integer from 1 to 4, or any number from 1 to 4 in a mixture, representing an average degree of polymerisation;

(b) a bis-secondary diamine radical such as a piperazine derivative of the formula:

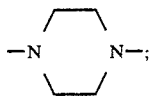

(c) a bis-primary diamine radical of the formula:

$$-NH-Y-NH-,$$

in which Y denotes a linear or branched hydrocarbon radical or the divalent radical $$-CH_2-CH_2-S-S-CH_2-CH_2-; \text{ or}$$

(d) a ureylene group of the formula $$-NH-CO-NH-;$$

and $X^-$ is an anion such as chloride or bromide.

These polymers generally have a molecular weight of 1,000 to 100,000.

Polymers of this type are described, in particular, in French Pat. Nos. 2,320,330, 2,270,846 and 2,316,271, French application Nos. 2,336,434 and 2,413,907 and U.S. Pat. Nos. 2,273,780, 2,375,853, 2,388,614, 2,454,547, 3,206,462, 2,261,002 and 2,271,378.

Other polymers of this type are described in U.S. Pat. Nos. 3,874,870, 4,001,432, 3,929,990, 3,966,904, 4,005,193, 4,025,617, 4,025,627, 4,025,653, 4,026,945 and 4,027,020.

(11) Homopolymers or copolymers derived from acrylic or methacrylic acid and containing the unit:

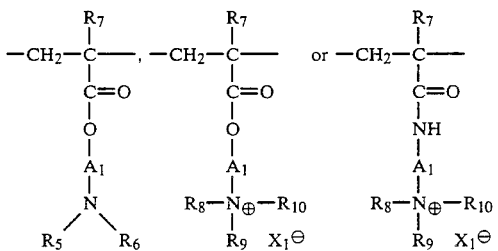

in which $R_7$ is H or $CH_3$, $A_1$ is a linear or branched alkylene group having up to 6 carbon atoms or a hydroxyalkylene group having 1 to 4 carbon atoms, $R_8$, $R_9$ and $R_{10}$, which are identical or different, represent an alkyl group having from 1 to 18 carbon atoms or a benzyl group, $R_5$ and $R_6$ represent hydrogen or an alkyl group having from 1 to 6 carbon atoms, and $X_1$ denotes a methosulphate anion or a halide such as chloride or bromide.

The comonomer or comonomers which can be used include: acrylamide, methacrylamide, diacetone-acrylamide, acrylamide and methacrylamide substituted on the nitrogen by one or more lower alkyls, alkyl esters of acrylic and methacrylic acids, vinylpyrrolidone and vinyl esters.

Examples which may be mentioned are:

the acrylamide/beta-methacryloyloxyethyl-trimethylammonium methosulphate copolymer sold under the names Reten 205, 210, 220 and 240 by Hercules, the ethyl methacrylate/oleyl methacrylate/beta-methacryloyloxyethyl-diethyl-methylammonium methosulphate copolymers listed under the name Quaternium 38 in the Cosmetic Ingredient Dictionary, the ethyl methacrylate/abietyl methacrylate/beta-methacryloyloxyethyl-diethyl-methylammonium methosulphate copolymer listed under the name Quaternium 37 in the Cosmetic Ingredient Dictionary, the beta-methacryloyloxyethyl-trimethylammonium bromide polymer listed under the name Quaternium 49 in the Cosmetic Ingredient Dictionary, the beta-methacryloyloxyethyl-trimethylammonium methosulphate/beta-methacryloyloxyethyl-stearyl-dimethylammonium methosulphate copolymer listed under the name Quaternium 42 in the Cosmetic Ingredient Dictionary, the aminoethylacrylate phosphate/acrylate copolymer sold under the name Catrex by National Starch, which has a viscosity of 700 cps at 25° C. in 18% strength aqueous solution, and graft crosslinked cationic copolymers, having a molecular weight of 10,000 to 1,000,000 and preferably of 15,000 to 500,000, which results from the copolymerisation of:

(a) at least one cosmetic monomer, (b) dimethylaminoethyl methacrylate, (c) polyethylene glycol and (d) a polyunsaturated crosslinking agent, these copolymers being described in French Pat. No. 2,189,434.

The crosslinking agent is typically ethylene glycol dimethacrylate, a diallyl phthalate, divinylbenzene, tetraallyloxyethane or polyallylsucrose having from 2 to 5 allyl groups per molecule of sucrose.

The cosmetic monomer can be of a very wide variety of types, for example a vinyl ester of an acid having from 2 to 18 carbon atoms, an allyl or methallyl ester of an acid having from 2 to 18 carbon atoms, an acrylate or methacrylate of a saturated alcohol having from 1 to 18 carbon atoms, an alkyl vinyl ether in which the alkyl radical contains from 2 to 18 carbon atoms, an olefine having from 4 to 18 carbon atoms, a vinylic heterocyclic derivative, a dialkyl or N,N-dialkylaminoalkyl maleate in which the alkyl radicals have from 1 to 3 carbon atoms, or the anhydride of an unsaturated acid.

(12) Quaternary vinylpyrrolidone/vinylimidazole polymers such as, for example, Luviquat FC 905 sold by B.A.S.F.

(13) Cationic silicone polymers, for example those described in European Applications Nos. 17,121 and 17,122, U.S. Pat. No. 4,185,087, Japanese patent application No. 80166,506 and Austrian patent application No. 71/01,171, and also those listed in the CTFA dictionary under the name AMODIMETHICONE, such as the product marketed as a mixture with other ingredients under the name "Dow Corning 929" cationic emulsion.

(14) Cationic derivatives of starches or of starch ethers, such as those described in French patent application No. 2,434,821, in particular the polymer sold under the name LAB 358 by ROQUETTE.

(15) Polyalkyleneimines.

(16) Polymers containing vinylpyridine units or vinylpyridinium units in the chain.

(17) Condensates of polyamines and epichlorohydrin.

(18) Chitin derivatives.

(19) Proteins and polypeptides of animal or vegetable origin, rendered cationic with a tertiary fatty amine.

The anionic polymers which can be used according to the invention are, in general, polymers containing one or more carboxylic, sulphonic or phosphoric acid groups. They generally have a molecular weight of 500 to 3,000,000.

The carboxyl groups can be introduced by means of unsaturated monocarboxylic or dicarboxylic acid represented, in particular, by the formula:

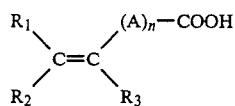

in which n is 0 or an integer from 1 to 10, A denotes a methylene group optionally joined to the carbon atom of the unsaturated group, or to the adjacent methylene group if n is greater than 1, via a heteroatom such as oxygen or sulphur, $R_1$ denotes a hydrogen atom or a phenyl or benzyl group, $R_2$ denotes a hydrogen atom or a lower alkyl or carboxyl group and $R_3$ denotes a hydrogen atom, a lower alkyl group, a group —CH$_2$—COOH or a phenyl or benzyl group.

In the abovementioned formula, a lower alkyl radical preferably denotes a group having 1 to 4 carbon atoms, and, in particular, methyl or ethyl.

The preferred anionic polymers according to the invention are chosen, in particular, from amongst:

Homopolymers or copolymers of acrylic or methacrylic acid or their salts, and in particular the products sold under the names VERSICOL E or K by ALLIED COLLOID, ULTRAHOLD 8 by CIBA GEIGY, DARVAN NO. 7 by Van Der BILT, VINAPOL 1640 by SHEBY and CARBOSET 514 by GOODRICH; the acrylic acid/acrylamide copolymers sold in the form of their sodium salts under the names RETEN 421, 423, or 425 by HERCULES; and the sodium salts of polyhydroxycarboxylic acids sold under the name HYDAGEN F by HENKEL.

Copolymers of the abovementioned acids with a monoethylenic monomer such as ethylene, vinylbenzene, a vinyl or allyl ester or an acrylic or methacrylic acid ester, optionally grafted onto a polyalkylene glycol such as polyethylene glycol, and optionally crosslinked. Such polymers are described, in particular, in French Pat. No. 1,222,944 and German application No. 2,330,956; and copolymers of this type containing an optionally N-alkylated and/or hydroxyalkylated acrylamide unit in their chain, such as described, in particular, in Luxembourg patent applications Nos. 75,370 and 75,371 or offered under the name QUADRAMER 5 by American Cyanamid.

Copolymers derived from crotonic acid, such as those containing, in their chain, vinyl acetate or propionate units and optionally other monomers such as allyl or methallyl esters, vinyl ether or the vinyl ester of a saturated carboxylic acid with a long hydrocarbon chain, such as those containing at least 5 carbon atoms, it being possible, if appropriate, for these polymers to be graft and crosslinked, or alternatively a vinyl, allyl or methallyl ester of an α- or β-cyclic carboxylic acid. Such polymers are described, inter alia, in French Pat. Nos. 1,222,944, 1,580,545, 2,265,782, 2,265,781, 1,564,110 and 2,439,798. Commercial products belonging to this class are the resins 28-29-30, 26-13-14 and 28-13-10 sold by National Starch.

Polymers derived from maleic, fumaric and itaconic acids or anhydrides with a vinyl ester, vinyl ether, vinyl halide, phenylvinyl derivative, acrylic acid or an ester thereof; these polymers can be esterified. Such polymers are described, in particular, in U.S. Pat. Nos. 2,047,398, 2,723,248 and 2,102,113 and British Pat. No. 839,805. There may be mentioned, in particular, the polymers sold under the names GANTREZ AN or ES by General Anilin or EMA 1325 by MONSANTO. Other polymers belonging to this class are copolymers of maleic, citraconic or itaconic anhydride and an allyl or methallyl ester, optionally copolymerised with another monomer such as an acrylamide, methacrylamide, olefine, vinyl ether, acrylic or methacrylic ester, acrylic or methacrylic acid, or N-vinylpyrrolidone, the anhydride groups being monoesterified or monoamidified as described in French Pat. Nos. 2,350,834 and 2,357,241.

Polyacrylamides containing carboxylate groups, such as those sold by American Cyanamid under the name CYANAMER A 370.

The polymers containing a sulphonic acid group which can be used according to the invention are chosen, in particular, from amongst:

Polystyrenesulphonic acid salts such as the sodium salts sold under the name Flexan 500, which has a molecular weight of about 500,000, or under the name Flexan 130, which has a molecular weight of about 100,000, by National Starch. Such compounds are described, in particular, in French Pat. No. 2,198,729.

Alkali metal or alkaline earth metal salts of the sulphonic acids derived from lignin, and more particularly calcium or sodium lignosulphonates such as the product sold under the name Marasperse C-21 by American Can Co. and the $C_1$–$C_{14}$ products sold by Avébène.

Polymers containing salified alkylnaphthalenesulphonic acid units, such as the sodium salt sold under the name Darvan No. 1 by Van der Bilt.

Polymers containing at least one vinylsulphonic acid unit, such as, more particularly, polyvinylsulphonates having a molecular weight of 1,000 to 100,000, and in particular their sodium, potassium, calcium and ammonium salts and the amine salts such as the alkylamine salts and alkanolamine salts, and also copolymers containing at least some vinylsulphonic acid groups with one or more cosmetically acceptable comonomers such as unsaturated acids chosen from acrylic and methacrylic acids and their esters, amides such as acrylamide or methacrylamide, which may or may not be substituted, vinyl esters, vinyl ethers and vinylpyrrolidone. These polymers are described more particularly in French Pat. No. 2,238,474 and U.S. Pat. Nos. 2,961,431 and 4,138,477.

It is also possible, according to the invention, to use amphoteric polymers in place of the cationic polymers or alternatively in place of the anionic polymers. In this case, it is compulsory to use amphoteric polymers either with an anionic polymer if the amphoteric polymer replaces the cationic polymer, or with a cationic polymer if the amphoteric polymer replaces the anionic polymer. The amphoteric polymers consist of units A and B randomly distributed in a polymer chain, where A denotes a unit derived from a monomer containing at least one basic nitrogen atom and B denotes a unit derived from an acid monomer containing one or more carboxylic or sulphonic acid groups, or, alternatively, A and B can denote groups derived from zwitterionic carboxybetaine monomers; A and B can also denote a cationic polymer chain containing secondary, tertiary or quaternary amino groups, in which at least one of the amino groups carries a carboxylic or sulphonic acid group joined via a hydrocarbon radical, or alternatively A and B form part of a chain of a polymer with an α,β-di-carboxyethylene unit, in which one of the carboxyl groups has been reacted with a polyamine containing one or more primary or secondary amine groups.

These polymers are described, in particular, in U.S. Pat. No. 3,836,537 and French Pat. Nos. 1,400,366, 2,252,840 and 2,368,508 and also in French patent application No. 2,180,006. It is also possible to use amphoteric polymers of betainised dialkylaminoalkyl meth(acrylate) or dialkyteminoalkyl(meth)-acrylamide containing the following units:

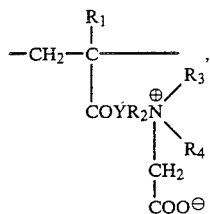

in which $R_1$ denotes a hydrogen atom or a methyl group, $R_2$ denotes an alkylene group having 1 to 4 carbon atoms, Y denotes 0 or NH and $R_3$ and $R_4$ independently of one another denote hydrogen or alkyl having 1 to 4 carbon atoms, and copolymers with units of acrylic or methacrylic acid esters containing alkyl radicals having 4 to 24 carbon atoms, or of acrylic or methacrylic acid esters containing alkyl radicals having 1 to 3 carbon atoms, and optionally one or more other monomers such as N-vinylpyrrolidone, acrylamide, hydroxyethyl or hydroxypropyl acrylate or methacrylate, acrylonitrile, styrene, chlorostyrene, vinyltoluene or vinyl acetate which copolymers are in themselves known.

For convenience, in the discussion reference is made to anionic and cationic polymers.

The compositions preferably contain the cationic or anionic polymers in an amount from 0.01 to 10% by weight relative to the total weight of the composition and, in particular, from 0.01 to 5% by weight relative to the total weight of the composition.

The preferred electrolytes which may be employed in the compositions according to the invention are salts of alkali metals and, particularly, sodium, potassium, or lithium salts of halides, such as chlorides or bromides, sulphates, carbonates or organic acid salts, such as acetates or lactates. In general, salt concentrations do not exceed 10% and are preferably from 0.5 to 5% by weight relative to the total weight of the composition.

The compositions applied in the first stage of the process according to the invention are generally presented in the form of aqueous solutions or solutions comprising a mixture of water and an alcohol, which solutions may or may not be thickened and which may be packaged in the form of an aerosol foam or spray.

It is obvious that these compositions can contain other adjuvants which are usually employed in the field of cosmetic compositions for the hair and, in particular, perfumes, dyestuffs, preservatives, sequestering agents, thickeners, non-ionic polymers or foam stabilisers, depending on the intended application.

Hair which has been treated and impregnated with the cationic and anionic polymers is kept in contact with them for up to, say, 30 minutes. After this period the hair is dried, normally with the aid of drying devices which are employed by a hairdresser for drying hair.

Immediately after drying, the dried hair is wetted or rinsed with an aqueous solution. This aqueous solution can consist simply of tap water.

A particularly preferred embodiment consists in applying to the dried hair an aqueous composition containing at least one cationic derivative which can be a cationic surface-active agent or a cationic polymer, or both. Such a procedure produces an appreciable increase in hair rigidity and markedly improves disentanglement.

The cationic derivatives which can be used in these rinsing compositions are generally quaternary nitrogen derivatives, fatty amines or fatty diamines. In this context, there may be mentioned alkyltrimethylammonium chlorides, bromides or para-toluenesulphonates, such as AKYPOQUAT 131, sold by DSM; dialkyldimethylammonium chlorides or bromides such as NORAMIUM M2SH and NORAMIUM M2C, sold by PIERREFITTE AUBY; alkylmethyldipolyoxyethyleneammonium chlorides such as ETHOQUAD C12, sold by ARMAK; dialkyldipolyoxyethyleneammonium sulphates, alkyltripolyoxyethyleneammonium chlorides or phosphates; polyoxypropylenemethyldiethylammonium chlorides, alkyldimethylhydroxyethylammonium chlorides, alkylpyridinium chlorides; alkylethylmorpholinium ethosulphates; alkylisoquinolinium chlorides or bromides; alkyldimethylbenzylammonium chlorides, bromides or saccharates; alkylbenzyltrimethylammonium chlorides; alkylbenzyltri(β-hydroxyethyl)ammonium chlorides; alkyldimethylalkylbenzylammonium cyclohexyl sulphamates; alkylxylyl-bis-(trimethylammonium) chlorides; alkyl(2-phenoxyethyl)ammonium bromides; alkylamidopropyldimethylhydroxyethylammonium chlorides; alkylamidopropyldiethylhydroxyethylammonium chlorides; or alkylamidopropyldimethylacetamidoammonium chlorides.

The salts of fatty amines or of fatty diamines are chosen particularly from the alkylamine acetates and hydrochlorides such as the product sold under the name CATIGENE JR by STEPAN; the alkylamidodiethylamines which have been solubilised by neutralisation, such as the products sold under the name MIRAMINE ST by MIRANOL or CHEMICAL BASE 6532 by SANDOZ; fatty diamines such as the products sold under the name CEMULCAT ODO-ODS by SFOS or INIPOL 002-SO2 by PIERREFITTE AUBY; fatty diamines which give soluble salts, sold under the name DINORAM C-S-O by PIERREFITTE AUBY, products of condensation of a fatty acid with hydroxyethylethylenediamine, sold particularly under the name CERANINE HC 39 B by SANDOZ; alkylamidoethylpolyhydroxyethylammonium hydrochlorides such as the product designated PC 735 sold by ATLAS, and ethylhydroxymethylalkyloxazolines such as ALKATERGE sold by IMC.

As cationic derivatives there can also be mentioned gluconamide quaternary halides as described in U.S. Pat. No. 3,766,267, cationic protein hydrolysates, mink oil amide quaternary halides as described in U.S. Pat. No. 4,012,398, quaternary derivatives of fatty halogenoalkanoates of dialkylaminopropylamide as described in U.S. Pat. No. 4,038,294, or quaternary ammonium derivatives of lanolin fatty acids as described in U.S. Pat. No. 4,069,347.

The cationic surface-active agents which are particularly preferred include distearyldimethylammonium chloride, stearyldimethylbenzylammonium chloride and alkyl-($C_{16}$–$C_{18}$)dimethylhydroxyethylammonium chloride and mixtures thereof.

The cationic polymers can be chosen from among the cationic polymers described above.

This composition can also contain an anionic polymer. The anionic polymers which can be employed are particularly those corresponding to the anionic polymer definition given above.

This composition can, of course, take the various forms of cosmetic compositions and can additionally contain cationic derivatives and/or cationic polymers, the adjuvents which are conventionally employed in cosmetics, such as perfumes, dyestuffs whose function may be to colour either the composition itself or the hair, preservatives, sequestering agents, thickeners, emulsifiers, non-cationic surfactants, softeners, electrolytes, non-ionic polymers, or foam stabilisers, according to the intended application.

These compositions can in particular be presented in the form of an aqueous solution, a solution which is a mixture of water and an alcohol which may or may not be thickened, a cream, gel, dispersion, emulsion, aerosol foam or spray.

These compositions can also be stored in the form of a freeze-dried powder to be diluted immediately before use with an appropriate liquid carrier.

The surfactants which can be employed in the compositions are typically present in an amount of 3 to 50%, and preferably 3 to 20% by weight; they can be surfactants which are commonly used for treating hair, including anionic, cationic, non-ionic, amphoteric or zwitterionic surfactants, and mixtures thereof.

These surface-active agents are themselves well known and are described in detail particularly in French Pat. No. 2,383,660.

The pH of these compositions is usually from 3 to 10.

When these compositions take the form of emulsions they can be non-ionic or anionic, the non-ionic emulsions consisting mainly of a mixture of oil and/or fatty alcohol and a polyethoxylated alcohol, such as polyethoxylated stearyl alcohol or polyethoxylated cetylstearyl alcohol. Cationic surfactants such as those specified above can be incorporated in these compositions.

The anionic emulsions consist substantially of soaps. When the compositions take the form of a thickened lotion or gel, they contain the thickeners which are present in the solvent. These thickeners can be, in particular, sodium alginate, gum arabic, or cellulose derivatives such as methylcellulose, hydroxymethylcellulose, hydroxyethylcellulose, hydroxypropylcellulose or hydroxypropylmethylcellulose. The lotions can also be thickened with a mixture of polyethylene glycol and polyethylene glycol stearate or polyethylene glycol distearate, or with a mixture of phosphoric ester and amide. The concentration of thickener is suitably 0.5 to 30% by weight and preferably 0.5 to 15% by weight.

The lotions are usually solutions in water, alcohol or a water-alcohol mixture.

Once it has been rinsed with one of these compositions, the hair can be rinsed with water, provided it has first been treated with a composition containing various cosmetically acceptable constituents such as described above. The hair is then set by means of conventional processes and dried.

A particularly preferred embodiment of the hair setting process consists in applying a composition containing at least one cationic polymer and at least one anionic polymer in a first stage, in drying the hair, in wetting or rinsing the hair, immediately after drying, with an aqueous composition containing at least one cationic compound and in setting the hairstyle.

The invention also relates to a process which consists in applying, as a composition for rinsing the dried hair in the second stage, a composition containing at least one cationic polymer.

Another embodiment consists in employing a composition containing a cationic polymer and an anionic polymer as a rinse composition.

Another variant of the process consists in employing a composition containing a cationic surfactant and a cationic polymer as a rinse composition. Finally, a particularly advantageous embodiment consists in applying, as the rinse composition, a composition containing a cationic surfactant, an anionic polymer and a cationic polymer, the cationic polymer being preferably a polyaminopolyamide which may be crosslinked, if appropriate, poly(quaternary ammonium) compounds and the cationic polymers of group 4 above.

The polymers which are particularly preferred in this embodiment of the invention are: in the case of cationic polymers vinylpyrrolidone/dialkylaminoalkyl acrylate or methacrylate copolymers of group 1 such as the product sold under the name GAFQUAT 755, cationic derivatives of cellulose ethers and cationic derivatives of cellulose of group 2 and particularly the products sold under the names JR 400 and CELQUAT L 200, cyclic polymers of group 9 and particularly the product sold under the name MERQUAT 550, poly-(quaternary ammonium) compounds of group 10 and particularly the polymer having recurring units of formula:

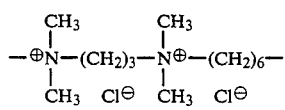

polyaminopolyamides of group 5 such as the polycondensate of ethylenetriamine and adipic acid, crosslinked with epichlorohydrin in a proportion of 11 moles of epichlorohydrin per 100 secondary amine groups in the polyaminoamide, piperazine polymers of group 4 such as the polycondensate of epichlorohydrin and piperazine, and in the case of anionic polymers
- polymers derived from maleic acid or maleic anhydride such as the polymer sold under the name GANTREZ ES 425,
- polyhydroxycarboxylic acid sodium salts such as those sold under the name HYDAGEN F,
- acrylic or methacrylic acid polymers such as those sold under the name VERSICOL E,
- sodium polyvinylsulphonates.

The preferred amphoteric polymers are betainised dialkylaminoalkyl (meth)acrylate polymers or dialkylaminoalkyl(meth)acrylamide polymers specified above.

The Examples which follow further illustrate the present invention.

EXAMPLE 1

| | |
|---|---|
| Polyamidopolyamine produced by the condensation of adipic acid and diethylenetriamine, followed by partial cross-linking with epichlorohydrin | 0.6 g AI* |
| Methyl vinyl ether/maleic anhydride copolymer monoesterified with butanol, sold at a concentration of 50% in ethanol under the name GANTREZ ES 425 by GAF | 0.4 g AI |
| Sodium chloride | 4 g |
| Water q.s. | 100 g |
| pH 7 with HCl | |

This composition is applied to hair after shampooing. The hair is then dried.

After drying and rinsing with water the hair is set and dried.

EXAMPLE 2

The lotion of Example 1 is applied to clean hair.

After a few minutes' application the hair is rinsed with water and then dried.

The hair is re-wetted and the following composition is then applied:

| | |
|---|---|
| Cationic cellulose sold under the name CELQUAT L 200 by National Starch | 0.4 g AI |
| Dimethyldistearylammonium compound | 0.4 g AI |
| Water q.s. | 100 g |
| pH 7 with NaOH | |

*AI = active ingredient

After a few minutes' application, the hair is rinsed with water, set and dried.

EXAMPLE 3

The following lotion is prepared:
Cationic polymer with recurring units of formula:

$$\left[ -N^{\oplus}(CH_3)_2 (CH_2)_3 N^{\oplus}(CH_3)_2 (CH_2)_6 - \right]_n \cdot 2nCl^-$$
0.5 g AI

| | |
|---|---|
| Polyacrylic acid (25% active ingredient) sold under the name VERSICOL E5 by ALLIED COLLOIDS | 1 g AI |
| NaCl | 4 g |
| Water, perfume, dyestuff, preservative qs | 100 g |
| pH = 7.2 with sodium hydroxide. | |

This composition is applied to hair after shampooing. The hair is dried. After drying it is rinsed with water and the hairstyle is set. The hair which has been set and then dried shows good shape-retention with time.

On rinsing the dried hair which has been treated with the above-mentioned lotion using the rinse composition of Example 2, a very good disentanglement is observed, and the dried hair shows good shape-retention after setting.

EXAMPLE 4

The following composition is applied to hair which has previously been treated with the composition of Example 1:

| | |
|---|---|
| Polymer resulting from the condensation of diethylenetriamine and adipic acid, partially crosslinked with epichlorohydrin | 1 g |
| Alkyldimethylhydroxyethylammonium chloride, in which the alkyl radical contains 16 to 18 carbon atoms | 0.4 g |
| Water, perfume, dyestuff, preservative q.s. | 100 g |
| pH = 7.1 with hydrochloric acid | |

It is found that the hair disentangles very easily after rising and that the dried hair shows great liveliness, firmness and shape-retention which persists for two to three weeks.

EXAMPLE 5

The following lotion is prepared:

| | |
|---|---|
| Sodium polyvinylsulphonate | 0.4 g AI |
| Polycondensate of epichlorohydrin and piperazine of molecular weight from 1,500 to 2,000 | 1 g AI |
| Na Cl | 4 g |
| Water, perfume, dyestuff, preservative q.s. | 100 g |
| pH 8.35 with hydrochloric acid. | |

This composition is applied to clean hair after shampooing and is rinsed and dried. The hair becomes firm.

The dried hair is rinsed with water and set. After drying it is found to have very good shape-retention with time and good disentanglement.

EXAMPLE 6

The following composition is applied to hair which has been treated with the composition of Example 5:

| | |
|---|---|
| Alkyldimethylhydroxyethylammonium chloride (alkyl radical having 16 to 18 carbon atoms) | 0.4 g |
| Water, perfume, dyestuff, preservative q.s. | 100 g |
| pH = 6.1 with hydrochloric acid | |

It is found that the wet hair disentangles very easily and that the dry hair is firm and lively.

EXAMPLE 7

The foam of the following composition, which has been packaged as an aerosol, is applied to clean hair:

| | |
|---|---|
| Quaternised cellulose sold under the name CELQUAT L 200 by National Starch | 0.6 g AI |
| Methyl vinyl ether/maleic anhydride copolymer monoesterified with butanol and sold at a concentration of 50% AI in | 0.4 g AI |

-continued

| | |
|---|---|
| ethanol by G.A.F. under the name GANTREZ ES 425 | |
| Ethanol | 6 g |
| Water, preservative q.s. | 100 g |
| The pH is adjusted to 7.5 with hydrochloric acid. | |

This composition is pressurised by using 90% by weight of the composition and 10% by weight of a propellant which is a mixture of Freons 12 and 114 in a proportion of 50/50 by weight.

After being rinsed and dried for a few minutes under a dryer the hair stiffens.

The following composition is then applied to damp hair:

| | |
|---|---|
| Silicone derivative which is sold at a concentration of 35% AI under the name Cationic Emulsion DC 929 by DOW CORNING | 1 g AI |
| Quaternary polyvinylpyrrolidone copolymer of molecular weight 1,000,000 sold under the name GAFQUAT 755 by GENERAL ANILINE | 0.3 g AI |
| Water, perfume, dyestuff, preservative q.s. | 100 g |
| The pH is adjusted to 7 with sodium hydroxide | |

It is found that, after rinsing, the hair is very soft and disentangles easily.

The dried hair has body.

EXAMPLE 8

The following composition, which is in the form of a lotion, is applied to unwashed hair:

| | |
|---|---|
| Adipic acid/dimethylaminohydroxypropyl-diethylenetriamine copolymer sold under the name CARTARETINE F4 by SANDOZ | 1.2 g AI |
| Maleic anhydride/methyl vinyl ether copolymer sold under the name GANTREZ AN 119 by G.A.F. | 0.6 g AI |
| Ethanol | 5 g |
| Water, preservative, dyestuff q.s. | 100 g |
| The pH is adjusted to 8.6 with sodium hydroxide. | |

After being rinsed and dried the hair stiffens.

The hair is then washed with the aid of the following composition:

| | |
|---|---|
| Quaternised cellulose sold under the name JR 400 by UNION CARBIDE | 1 g AI |
| Non-ionic surfactant of the formula: R—CHOH—CH$_2$—(CH$_2$CHOH—CH$_2$—O)$_{\overline{n}}$—H R is a mixture of C$_3$-C$_{12}$ alkyl radicals n is a statistical mean value of approximately 3.5 | 10 g AI |
| Water, perfume, dyestuff, preservative q.s. | 100 g |
| pH adjusted to 6 with sodium hydroxide. | |

This composition is applied to the hair, forming a copious foam which is easily removed.

The damp hair disentangles very easily whilst the dried hair is lively, has body and is firm.

EXAMPLE 9

The following composition, which is in the form of a gel, is applied to clean hair:

| | |
|---|---|
| Maleic anhydride/methyl vinyl ether copolymer sold under the name GANTREZ | 2.5 g AI |

-continued

| | |
|---|---|
| AN 149 by G.A.F. | |
| Polycondensate of epichlorohydrin, piperazine and diglycolamine | 0.9 g AI |
| Water, dyestuff, preservative, q.s. | 100 g |
| The pH is adjusted to 7.2 with sodium hydroxide. | |

After being dried the hair stiffens.

A foam with the following composition, which is packaged as an aerosol, is then applied:

| | |
|---|---|
| Distearyldimethylammonium chloride | 1.5 g AI |
| Quaternised protein derivative sold under the name LEXEIN CP 125 BY INDLEX | 0.65 g AI |
| Water, perfume, dyestuff, preservative, q.s. | 100 g |
| The pH is adjusted to 6.3 with sodium hydroxide | |

This composition is pressurised in a proportion of 90% by weight of composition to 10% by weight of a propellant which consists of a mixture of Freon 12 and Freon 114 in proportions of 50/50 by weight.

After being rinsed, the hair disentangles easily and the dried hair is shiny, lively and has body.

EXAMPLE 10

The following composition, which is packaged in the form of a spray, is applied to clean hair:

| | |
|---|---|
| Quaternary polyvinylpyrrolidone copolymer of molecular weight 1,000,000 sold under the name GAFQUAT 755 by GENERAL ANILINE | 0.8 g AI |
| Carboxylated vinyl acetate terpolymer sold under the name Resin 28 29 30 by NATIONAL STARCH | 0.4 g AI |
| Ethanol | 4 g |
| Water, perfume, dyestuff, preservative q.s. | 100 g |
| The pH is adjusted to 6.9 with sodium hydroxide. | |

This composition is pressurised in a proportion of 50% by weight of composition to 50% by weight of Freon 12.

After the hair is dried, the following composition, which is in the form of a gel, is applied to damp hair:

| | |
|---|---|
| Copolymer of dimethyldiallylammonium chloride and acrylamide of molecular weight greater than 500,000 sold under the name MERQUAT 550 by MERCK | 0.25 g |
| Ethylene oxide/propylene glycol polycondensate of average molecular weight 14,000 sold under the name PLURONIC F108 by UGINE KUHLMANN | 10 g AI |
| Water, perfume, preservative, dyestuff q.s. | 100 g |
| The pH is adjusted to 4.6 with sodium hydroxide. | |

EXAMPLE 11

A gel having the following composition is applied to unwashed hair:

| | |
|---|---|
| Amphoteric polymer sold under the name AMPHOSET by MITSUBISHI PETROCHEMICAL (a product of 50% strength in ethanol) | 0.3 g AI |
| Partially neutralised poly(hydroxycarbox- | 0.7 g AI |

-continued

| | |
|---|---|
| ylic) acid sold under the name HYDAGEN F by HENKEL | |
| Ethylene/maleic anhydride copolymer sold under the name EMA 91 by MONSANTO | 2 g AI |
| Water, perfume, preservative, dyestuff q.s. | 100 g |
| The pH is adjusted to 6.4 with sodium hydroxide. | |

After being dried, the hair is washed with the following composition:

| | |
|---|---|
| Glucoside alkylether sold at 30% AI under the name TRITON CG 110 by SEPPIC | 10 g AI |
| Cetyldimethylamine oxide sold at 30% AI under the name AMMONYX Co. by ONYX | 1 g AI |
| Distearyldimethylammonium chloride | 0.3 AI |
| Water, perfume, dyestuff, preservative q.s. | 100 g |
| The pH is adjusted to 7.6 with sodium hydroxide. | |

EXAMPLE 12

A foam of the following composition is applied to unwashed hair:

| | |
|---|---|
| Methyl vinyl ether/maleic anhydride copolymer monoesterified with butanol, sold at a concentration of 50% AI in ethanol under the name GANTREZ ES 425 by G.A.F. | 1 g AI |
| Surface-active agent off the formula: R—CHOH—CH$_2$—(CH$_2$CHOH—CH$_2$—O)$_n$—H R is a mixture of C$_9$-C$_{12}$ alkyl radicals n is a statistical mean value of approximately 3.5 | 0.5 g AI |
| Water, perfume, preservative, q.s. | 100 g |
| The pH is adjusted to 7.5 with sodium hydroxide. | |

This composition is pressurised in a proportion of 90% by weight of composition to 10% by weight of a propellant consisting of a 50/50 mixture of Freon 12 and Freon 114.

After a few minutes drying, the hair is washed with the help of the following composition:

| | |
|---|---|
| Surface-active agent of the formula: R—CHOH—CH$_2$—O—(CH$_2$CHOH—CH$_2$O)$_n$H R is a mixture of C$_9$-C$_{12}$ alkyl radicals n is a statistical mean value of approximately 3.5 | 10 g AI |
| Quaternised cellulose derivative sold under the name JR 400 by UNION CARBIDE | 1 g AI |
| Sodium chloride | 4 g |
| Water, perfume, dyestuff, preservative q.s. | 100 g |
| The pH is adjusted to 7.5 with sodium hydroxide. | |

After being rinsed the hair is dried, wetted and set.

The various patents and applications mentioned in this specification are hereby incorporated by reference.

We claim:

1. A hair-setting process, which comprises first treating the hair with at least one cationic polymer and at least one anionic polymer, in a solvent medium selected from the group consisting of water and a mixture of water and alcohol; drying the hair; and immediately after drying the hair, wetting or rinsing the hair with an aqueous composition; and then setting and drying the hair, said aqueous composition being selected from the group consisting of (1) water, (2) a mixture of water and a cationic polymer, (3) a mixture of water and a cationic surface-active agent, (4) a mixture of water, a cationic polymer and a cationic surface-active agent, (5) a mixture of water, a cationic polymer and an anionic polymer, (6) a mixture of water, a cationic surface-active agent and an anionic polymer, and (7) a mixture of water, a cationic polymer, a cationic surface-active agent and an anionic polymer.

2. A process according to claim 1, in which first a composition containing a cationic polymer in a solvent medium and then a composition containing an anionic polymer in a solvent medium are applied successively to the hair without intervening rinsing.

3. A process according to claim 1, in which first a composition containing an anionic polymer in a solvent medium and then a composition containing a cationic polymer are applied to the hair without intervening rinsing.

4. A process according to claim 1 in which the composition(s) first applied also contain(s) at least one salt of an alkali metal or of an alkaline-earth metal.

5. A process according to claim 4, in which the salt is a halide, sulphate, carbonate, acetate or lactate of sodium, potassium or lithium.

6. A process according to claim 1, in which a composition containing an anionic polymer, a cationic polymer and an electrolyte, without a surface-active agent, is first applied to the hair.

7. A process according to claim 1, in which the aqueous composition applied after drying contains at least one cationic derivative selected from the group consisting of a cationic surfactant and a cationic polymer.

8. A process according to claim 7, in which the cationic surfactant is a quaternary nitrogen derivative, fatty amine or fatty diamine.

9. A process according to claim 1 in which the aqeuous composition applied after drying contains an anionic polymer.

10. A process according to claim 1 in which the aqueous composition applied after drying contains a cationic surfactant, a cationic polymer and an anionic polymer.

11. A process according to claim 1 in which the aqueous composition applied after drying further contains at least one of a perfume, dyestuff, preservative, sequestering agent, thickener, emulsifier, non-cationic surface-active agent, softener, electrolyte and foam stabiliser.

12. A process according to claim 1 in which the aqueous composition applied after drying is in the form of a solution in water or a solution in a mixture of water and an alcohol.

13. A process according to claim 1 in which the hair is wetted with an aqueous composition containing at least one cationic derivative after being dried and then rinsed with water, set and dried.

14. A process according to claim 1 in which the hair is rinsed after the first treatment and before being dried.

15. A process according to claim 1 in which the cationic polymer or anionic polymer is present in the respective composition in an amount from 0.1 to 10% by weight relative to the total weight of the composition.

16. A process according to claim 1 in which the cationic polymer has a molecular weight of 500 to 3,000,000 and is a polyamine, polyaminopolyamide or poly-(quaternary ammonium) polymer.

17. A process according to claim 16, in which the cationic polymer is chosen from:

(1) a quaternised or unquaternised vinylpyrrolidone/-dialkylaminoalkyl acrylate or methacrylate copolymer;
(2) a cellulose ether derivative containing quaternary ammonium groups, or a quaternary cellulose derivative;
(3) a cationic polysaccharide;
(4) a cationic polymer which is a polymer containing units of the formula $$-A-Z-A-Z-  \quad (I),$$

in which A denotes a radical containing two amino groups, and Z deontes the synbol B or B', B and B', which are identical or differrent, denoting a linear or branched alkylene radical which is unsubstituted or substituted by one or more hydroxyl groups and which can also contain one or more oxygen, nitrogen or sulphur atoms and 1 to 3 aromatic and/or heterocyclic rings; a polymer containing units of the formula $$-A-Z_1-A-Z_1-  \quad (II),$$

in which A is as defined above and $Z_1$ denotes the symbol $B_1$ or $B'_1$, at least one $Z_1$ denoting $B'_1$, $B_1$ being a linear or branched alkylene or hydroxyalkylene radical and $B'_1$ being a linear or branched alkylene radical which is unsubstituted or substituted by one or more hydroxyl radicals and which is interrupted by one or more nitrogen atoms which are substituted by an alkyl radical which is optionally interrupted by a chain oxygen atom and which optionally contains one or more hydroxyl groups; or a quaternary ammonium salt or oxidation product of a polymer containing units of the formula (I) or (II);
(5) a polyaminopolyamide;
(6) a crosslinked polyaminopolyamide which is:
 (a) an optionally alkylated, crosslinked polyaminopolyamide obtained by crosslinking a polyaminopolyamide prepared by the polycondensation of an acid with a polyamine, with a crosslinking agent which is an epihalogenohydrin, diepoxide, dianhydride, unsaturated anhydride or bis-unsaturated derivative, the crosslinking agent being used in an amount from 0.025 to 0.35 mol per amine group of the polyaminopolyamide;
 (b) a water-soluble crosslinked polyaminopolyamide obtained by crosslinking a polyaminopolyamide as defined above with a crosslinking agent which is:
  (I) a bis-halogenohydrin, bis-azetidinium compound, bis-halogenoacyldiamine or bis-(alkyl halide),
  (II) an oligomer obtained by reacting a compound from group I or an epihalogenohydrin, diepoxide or bis-unsaturated derivative with a difunctional compound reactive thereto, or
  (III) a quaternisation product of a compound from group I or an oligomer from group II, containing tertiary amine groups which can be totally or partially alkylated, with an alkylating agent.
  the crosslinking being carried out using 0.025 to 0.35 mol of crosslinking agent per amine group of the polyaminopolyamide; or
 (c) a polyaminopolyamide derivative resulting from the condensation of a polyalkylene-polyamine with a polycarboxylic acid, followed by alkylation with a difunctional agent (7) a polymer obtained by reacting a polyalkylene-polyamine containing two primary amino groups and at least one secondary amino group with a dicarboxylic acid which is diglycolic acid or a saturated aliphatic dicarboxylic acid having 3 to 8 carbon atoms, the molar ratio of the polyalkylene-polyamino to the dicarboxylic acid being from 0.8:1 to 1.4:1, and the resulting polyaminopolyamide being reacted with epichlorohydrin in a molar ratio of epichlorohydrin to the secondary amino groups of the polyaminopolyamide of from 0.5:1 to 1.8:1;
(8) a cyclic polymer containing units corresponding to the formula (III) or (III')

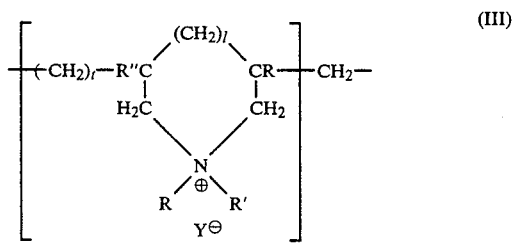
(III)

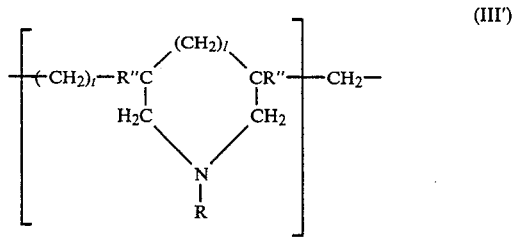
(III')

in which l and t are equal to 0 or 1 such that l=t=1, R'' denotes hydrogen or methyl, R and R' independently of one another denote an alkyl group having 1 to 22 carbon atoms, a hydroxyalkyl group or a lower amidoalkyl group, or R and R' denote, together with the nitrogen atom to which they are attached, a heterocyclic group, or a copolymer containing units of the formula (III) or (III') and units derived from acrylamide or from diacetone-acrylamide, and $Y^\ominus$ is an anion;
(9) a poly-(quaternary ammonium) compound comprising recurring units of the formula:

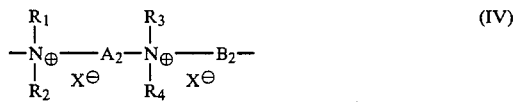
(IV)

in which $R_1$ and $R_2$, and $R_3$ and $R_4$, which are identical or different, represent an aliphatic, alicyclic or arylaliphatic radical containing at most 20 carbon atoms, or a lower hydroxyaliphatic radical, or alternatively $R_1$ and $R_2$, and/or $R_3$ and $R_4$, together form, with the nitrogen atom to which they are attached, a heterocyclic ring optionally containing a second heteroatom other than nitrogen, or $R_1$, $R_2$, $R_3$ and $R_4$ independently represent a group of the formula:

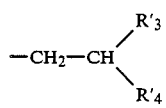

R′3 denoting hydrogen or lower alkyl and R′4 denoting:

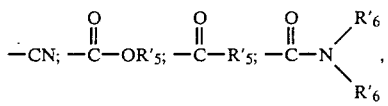
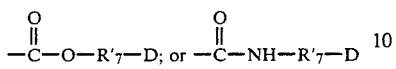

R′5 denoting lower alkyl, R′6 denoting hydrogen or lower alkyl, R′7 denoting alkylene and D denoting a quaternary ammonium group, A2 and B2 independently an aliphatic group containing from 2 to 20 carbon atoms, which can be linear or branched and saturated or unsaturated and which can contain, in the chain, one or more aromatic rings of the formula:

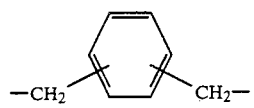
(o, m or p)

or one or more groups of the formula:

—(CH2)$_n$—Y1—(CH2)$_n$—, with Y1 denoting O, S, SO, SO2,

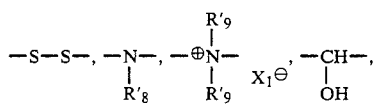
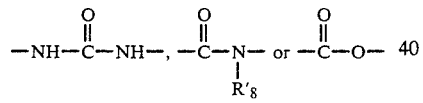

with X$^\ominus$1 denoting an anion derived from a mineral or organic acid, n being 2 or 3, R′8 denoting hydrogen or lower alkyl and R′9 denoting lower alkyl, or alternatively A2 and R1 and R3 together form a piperazine ring with the nitrogen atoms to which they are attached; such that if A2 denotes a linear or branched, saturated or unsaturated aliphatic or hydroxy-aliphatic radical, B2 can also denote a group of the formula:

—(CH2)$_n$—CO—D—OC—(CH2)$_n$, in which D denotes:
(a) a glycol radical of the formula

—O—Z—O—, in which Z denotes a linear or branched hydrocarbon radical or a group corresponding to the formula:

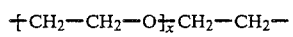

or

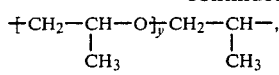

in which x and y denote an integer from 1 to 4;
(b) a bis-secondary diamine radical;
(c) a bis-primary diamine radical of the formula:

—NH—Y—NH—, in which Y denotes a linear or branched hydrocarbon radical or the divalent radical —CH2—CH2—S—S—CH2—CH2—; or
(d) a ureylene group of the formula

—NH—CO—NH—;

X$^-$ denotes an anion, the compound having a molecular weight from 1,000 to 100,000;
(10) a homopolymer or copolymer derived from acrylic or methacrylic acid and containing at least one recurring unit of the formula:

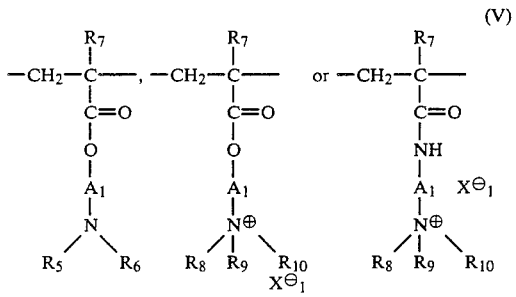
(V)

in which R7 is H or CH3, A1 is a linear or branched alkyl group having 1 to 6 carbon atoms or a hydroxyalkyl group having 1 to 4 carbon atoms, R8, R9 and R10, which are identical or different, denote an alkyl group having 1 to 18 carbon atoms or a benzyl group, R5 and R6 denote H or alkyl having 1 to 6 carbon atoms, and X$^\ominus$1 denotes a methosulphate or halide anion;
(11) a quaternary vinylpyrrolidone/vinylimidazole copolymer;
(12) a polyalkyleneimine;
(13) a polymer containing chain vinylpyridine or vinylpyridinium units;
(14) a condensate of a polyamine and epichlorohydrin;
(15) a poly-(quaternary ureylene) compound;
(16) a chitin derivative;
(17) a protein or polypeptide of animal or vegetable origin, rendered cationic with a tertiary fatty amine;
(18) a cationic silicone polymer; or
(19) a cationic derivative of starch or a starch ether.
18. A process according to claim 1, in which the anionic polymer contains one or more carboxylic, sulphonic or phosphoric acid groups and has a molecular weight of 500 to 3,000,000.
19. A process according to claim 18 in which the polymer containing a carboxylic acid group is derived from the unsaturated monocarboxylic or dicarboxylic acid represented by the formula:

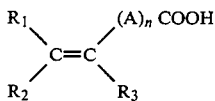

in which n is 0 or an integer from 1 to 10, A denotes a methylene group optionally joined to the carbon atom of the unsaturated group, or to the adjacent methylene group if n is greater than 1, via a heteroatom, $R_1$ denotes a hydrogen atom or a phenyl or benzyl group, $R_2$ denotes a hydrogen atom or a lower alkyl or carboxyl group and $R_3$ denotes a hydrogen atom, a lower alkyl group, a group —$CH_2$—COOH or a phenyl or benzyl group, the polymer containing a sulphonic acid group is a polystyrenesulphonic acid salt, an alkali metal or alkaline earth metal salt of a sulphonic acid derived from lignin, a polymer containing salified alkylnaphthalenesulphonic acid units, or a polymer containing vinylsulphonic units.

20. A process according to claim 1, in which an amphoteric polymer and an anionic polymer are first applied to the hair.

21. A process according to claim 1, in which an amphoteric polymer and a cationic polymer are first applied to the hair.

22. A process according to claim 20, in which the amphoteric polymer consists of units A and B randomly distributed in a polymer chain, wherein A denotes a unit derived from a monomer containing at least one basic nitrogen atom and B denotes a unit derived from an acid monomer containing one or more carboxylic or sulphonic acid groups.

23. A process according to claim 1 wherein said solution is thickened.

24. A process according to claim 1 wherein said solution is packaged in the form of an aerosol foam.

25. A process according to claim 1 wherein said solution is thickened and packaged in the form of an aerosol foam.

26. A process according to claim 12 wherein said aqueous composition is in a form selected from the group consisting of a thickened solution, a cream, a gel, a dispersion, an emulsion, an aerosol foam, and an aerosol spray.

27. A hair setting process which comprises first treating the hair with a solvent medium containing a cationic polymer which has a molecular weight of 500 to 3,000,000, said cationic polymer being selected from the group consisting of a polyamine, a polyaminopolyamide, and a poly-(quaternary ammonium) polymer; and at least one anionic polymer having a molecular weight of 500 to 3,000,000, said anionic polymer containing one or more carboxylic, sulphonic or phosphoric acid groups, said solvent medium being selected from the group consisting of water and a mixture of water and alcohol; drying the hair; and immediately after drying the hair, wetting or rinsing the hair with an aqueous composition; and then setting and drying the hair, said aqueous composition being selected from the group consisting of (1) water, (2) a mixture of water and a cationic polymer, (3) a mixture of water and a cationic surface-active agent, (4) a mixture of water, a cationic polymer and a cationic surface-active agent, (5) a mixture of water, a cationic polymer and an anionic polymer, (6) a mixture of water, a cationic surface-active agent and an anionic polymer, and (7) a mixture of water, a cationic polymer, a cationic surface-active agent and an anionic polymer.

28. A hair setting process, which comprises first treating the hair with at least one of a cationic polymer and an anionic polymer, and an amphoteric polymer in a solvent medium selected from the group consisting of water and a mixture of water and alcohol; drying the hair; and immediately after drying the hair, wetting or rinsing the hair with an aqueous composition; and then setting and drying the hair, said aqueous composition being selected from the group consisting of (1) water, (2) a mixture of water and a cationic polymer, (3) a mixture of water and a cationic surface-active agent, (4) a mixture of water, a cationic polymer and a cationic surface-active agent, (5) a mixture of water, a cationic polymer and an anionic polymer, (6) a mixture of water, a cationic surface-active agent and an anionic polymer, and (7) a mixture of water, a cationic polymer, a cationic surface-active agent and an anionic polymer.

29. A process according to claim 22 in which the amphoteric polymer consists of units A and B randomly distributed in a polymer chain, wherein A and B denote groups derived from one or more zwitterionic carboxybetaine monomers.

30. A process according to claim 22 in which the amphoteric polymer consists of units A and B randomly distributed in a polymer chain, wherein A and B denote a cationic polymer chain containing secondary, tertiary or quaternary amino groups, in which at least one of the amino groups carries a carboxylic or sulphonic acid group joined via a hydrocarbon radical.

31. A process according to claim 22 in which the amphoteric polymer consists of units A and B randomly distributed in a polymer chain, wherein A and B form part of a chain of a polymer with an $\alpha,\beta$-dicarboxyethylene unit, in which one of the carboxyl groups has been reacted with a polyamine containing one or more primary or secondary amine groups.

32. A hair setting process which comprises first treating the hair with a solvent medium containing at least one of a cationic polymer which has a molecular weight of 500 to 3,000,000, said cationic polymer being selected from the group consisting of a polyamine, a polyaminopolyamide, and a poly-(quaternary ammonium) polymer and an anionic polymer having a molecular weight of 500 to 3,000,000, said anionic polymer containing one or more carboxylic, sulphonic or phosphoric acid groups; and an amphoteric polymer, said amphoteric polymer consisting of units A and B randomly distributed in a polymer chain, wherein A denotes a unit derived from a monomer containing at least one basic nitrogen atom and B denotes a unit derived from an acid monomer containing one or more carboxylic or sulphonic acid groups, said solvent medium being selected from the group consisting of water and a mixture of water and alcohol; drying the hair; and immediately after drying the hair, wetting or rinsing the hair with an aqueous composition; and then setting and drying the hair, said aqueous composition being selected from the group consisting of (1) water, (2) a mixture of water and a cationic polymer, (3) a mixture of water and a cationic surface-active agent, (4) a mixture of water, a cationic polymer and a cationic surface-active agent, (5) a mixture of water, a cationic polymer and an anionic polymer, (6) a mixture of water, a cationic surface-active agent and an anionic polymer, and (7) a mixture of water, a cationic polymer, a cationic surface-active agent and an anionic polymer.

33. A hair setting process according to claim 32 wherein A and B denote groups derived from one or more zwitterionic carboxybetaine monomers.

34. A hair setting process according to claim 32 wherein A and B denote a cationic polymer chain containing secondary, tertiary or quaternary amino groups, in which at least one of the amino groups carries a carboxylic or sulphonic acid group joined via a hydrocarbon radical.

35. A hair setting process according to claim 32 wherein A and B form part of a chain of a polymer with an $\alpha,\beta$-dicarboxyethylene unit, in which one of the carboxyl groups has been reacted with a polyamine containing one or more primary or secondary amine groups.

* * * * *